United States Patent [19]

Grollier et al.

[11] Patent Number: 4,668,237
[45] Date of Patent: May 26, 1987

[54] DYE COMPOSITION CONTAINING 5-NITROVANILLIN AND ITS USE FOR DYEING KERATINIC FIBRES, AND ESPECIALLY HUMAN HAIR

[75] Inventors: Jean F. Grollier, Paris; Jean Cotteret, Limay; Georges Rosenbaum, Asnieres, all of France

[73] Assignee: L'Oreal, Paris, France

[21] Appl. No.: 812,638

[22] Filed: Dec. 23, 1985

[30] Foreign Application Priority Data

Dec. 21, 1984 [LU] Luxembourg ............ 85704

[51] Int. Cl.$^4$ .................. A61K 7/13; C07C 79/36
[52] U.S. Cl. .............................. 8/424; 8/405; 8/415; 8/429; 568/424
[58] Field of Search ............ 8/424, 405, 415, 414; 568/424

[56] References Cited

U.S. PATENT DOCUMENTS

4,305,717  12/1981  Bugaut et al. ............ 8/411
4,470,826   8/1984  Bugaut et al. ............ 8/115

FOREIGN PATENT DOCUMENTS

464312  6/1975  U.S.S.R. .

OTHER PUBLICATIONS

Tamari et al, "Agent for Prevention of Infection of Firicularia Orzyzae on Rice" Japan 3, 198('61) Apr. 14, Appl. Mar. 7, 1957.

Prager et al, *Beilsteins Handbook of Organic Chemistry*, vol. VIII, 5-Nitro-4-hydroxy-3 methoxy-benzaldehyde, pp. 161-162.

*Primary Examiner*—Paul Lieberman
*Assistant Examiner*—L. Skaling
*Attorney, Agent, or Firm*—Cushman, Darby & Cushman

[57] ABSTRACT

The invention relates to a composition for dyeing keratinic fibres, especially human hair, which contains 5-nitrovanillin of formula:

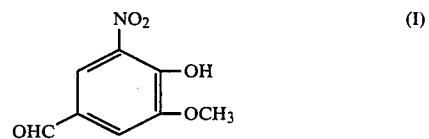

in an aqueous, alcoholic or hydroalcoholic carrier.

This yellow nitro dye makes it possible to obtain stable shades having good light- and shampoo-resistance when it is used by itself or in combination with blue or violet nitrobenzene dyes, and optionally with other direct dyes.

20 Claims, No Drawings

DYE COMPOSITION CONTAINING 5-NITROVANILLIN AND ITS USE FOR DYEING KERATINIC FIBRES, AND ESPECIALLY HUMAN HAIR

The present invention relates to new compositions for dyeing keratinic fibres, which contain 5-nitrovanillin, and to the use of the said compositions for dyeing keratinic fibres, and especially human hair.

In the field of hair-dyeing it is well known to use dyes known as oxidation dyes, which are technically highly effective owing to the fact that they produce shades which mask very well and are fast. However, these dyes give rise to the phenomenon of a boundary between the dyed ends and mid-lengths and the undyed roots, due to the regrowth of hair.

Consequently, increasing use is being made of direct dyes which, by virtue of the diversity of possible substituents, enable a wide range of shades to be covered, ranging from yellow to blue via red, without the need for bleaching the hair. This, combined with the fact that they are less fast to washing, results in the disappearance of the boundary phenomenon due to fresh growth.

Furthermore, these direct dyes and more precisely the nitrobenzene dyes, which are the most effective, are also tolerated very well.

However, direct dyes are not free from disadvantages. They are criticized, inter alia, for being inadequately fast to washing and to light.

In the course of their investigations, the applicants have found that 5-nitrovanillin, which has the formula:

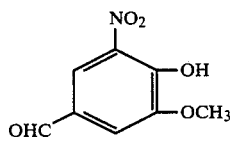
(I)

could be used as a yellow nitrobenzene dye in the usual dye carriers and enabled a shade having good light- and shampoo-resistance to be imparted to keratinic fibres.

Furthermore, 5-nitrovanillin has the advantage of good stability in solution, even at alkaline pH, despite the presence of the aldehyde group.

A subject of the present invention is consequently a dye composition for dyeing keratinic fibres, and especially human hair, which contains 5-nitrovanillin of formula (I) indicated above, in an aqueous, alcoholic or hydroalcoholic carrier.

The dye composition according to the invention contains 0.01 to 1% by weight of 5-nitrovanillin of the above formula (I).

In addition, the applicants have found that when it is used to dye hair, 5-nitrovanillin has an enhanced selectivity compared to the conventional yellow direct nitrobenzene dyes.

The selectivity of a dye is the name given to the difference in the latter's ascent on the capillary fibre depending on whether the latter is sensitized to a greater or lesser degree by a treatment such as bleaching or permanent-waving.

Many nitrobenzene dyes have a very different ascent on hair according to the degree of hair sensitization. This is especially the case with nitro-paraphenylenediamines disubstituted on the amino group in a position meta to the nitro group, which form blue or violet dyes enabling natural, or naturally-highlighted shades to be obtained when they are used in combination with yellow or green-yellow dyes.

It is consequently of great importance that the blue or violet nitro dyes and the yellow or green-yellow dyes should behave similarly on a hair which is variously sensitized from the root to the end, especially after a permanent-wave treatment.

In the case where this requirement is not met, a head of hair which has regions of unequal sensitization (for example on the lengths and at the ends) will show either an excessively violet tone at the ends and an excessively matt tone over the lengths, or the opposite, depending on the balance of dyes chosen by the formulator.

Until now, the ideal balance was difficult to achieve with the conventional yellow direct nitrobenzene dyes, because dyes of this type which were used until now are not as sensitive to permanent-waving as the blue or violet direct benzene dyes introduced into the dyeing compositions.

As a result, by virtue of its enhanced selectivity on sensitized hair, 5-nitrovanillin can be advantageously used as a yellow dye in compositions for dyeing keratinic fibres, and especially human hair, in combination with blue or violet nitrobenzene dyes of formula:

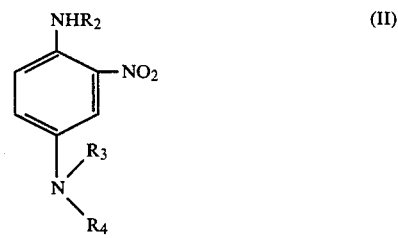
(II)

in which $R_2$ denotes a hydrogen atom, a lower alkyl radical containing 1 to 4 carbon atoms, or a $C_1$-$C_4$ monohydroxyalkyl or a $C_2$-$C_4$ polyhydroxyalkyl radical, and $R_3$ and $R_4$ have individually the same meanings as $R_2$, but cannot denote a hydrogen atom.

According to a preferred embodiment, the dyeing composition according to the invention contains, therefore, 5-nitrovanillin of formula (I) in combination with at least one violet or blue nitrobenzene dye of the above formula (II).

Among the blue or violet nitrobenzene dyes of formula (II) which are preferably used according to the invention, there may be mentioned, without this list being of a limiting nature:

2-(N-methyl)amino-5-[N,N-bis($\beta$-hydroxyethyl)amino]nitrobenzene;

2-(N-methyl)amino-5-[N-methyl-N-($\beta$-hydroxyethyl)amino]nitrobenzene;

2-(N-$\beta$-hydroxyethyl)amino-5-[N,N-bis($\beta$-hydroxyethyl)amino]nitrobenzene;

2-(N-$\beta$-hydroxyethyl)amino-5-[N-methyl-N-($\beta$-hydroxyethyl)amino]nitrobenzene;

2-(N-$\gamma$-hydroxypropylamino)-5-[N,N-bis($\beta$-hydroxyethyl)amino]nitrobenzene;

2-(N-methylamino)-5-(N-methhyl-N-($\beta,\gamma$-dihydroxypropyl)amino]-nitrobenzene; and 2-amino-5-[N,N-bis($\beta$-hydroxyethyl)amino]nitrobenzene.

In the case where the dye composition according to the invention contains the violet or blue dyes of above formula (II), the latter represent 0.01 to 5% of the total weight of the composition.

It is also possible, of course, to use 5-nitrovanillin of formula (I) in combination with other direct dyes, in the presence or in the absence of blue or violet nitrobenzene dyes of formula (II).

In this case, the other direct dyes are either nitrobenzene derivatives other than the yellow dye of formula (I) or blue or violet dyes of formula (II), or are azo, aminoanthraquinone, metallized, triarylmethane derived, or indamine dyes.

These other direct dyes can represent between 0.001 and 10% of the total weight of the composition.

Among the nitrobenzene derivatives other than the compounds of formula (I), or (II), there may be mentioned yellow, orange or red dyes belonging either to the nitro-para-phenylenediamine series or to other series of nitrobenzene dyes, for example nitroaminophenols, nitroaminoalkoxybenzenes, and nitroaminohydroxyalkoxybenzenes. Among these dyes, there may be mentioned, without implying any limitation;

2-amino-5-N-methylaminonitrobenzene,
2,4-diaminonitrobenzene,
3,4-diaminonitrobenzene,
2,5-diaminonitrobenzene,
3-amino-4-hydroxynitrobenzene,
3-hydroxy-4-aminonitrobenzene,
2-hydroxy-5-aminonitrobenzene,
2-amino-5-hydroxynitrobenzene,
2-amino-3-hydroxynitrobenzene,
2-amino-5-N-($\beta$-hydroxyethyl)aminonitrobenzene,
2-N-($\beta$-hydroxyethyl)amino-5-hydroxynitrobenzene,
3-methoxy-4-N-($\beta$-hydroxyethyl)aminonitrobenzene,
2-N-methylamino-4-($\beta$-hydroxyethyloxy)nitrobenzene,
2-amino-3-methylnitrobenzene,
2-N-($\beta$-hydroxyethyl)amino-5-aminonitrobenzene,
2-amino-4-chloro-5-N-($\beta$-hydroxyethyl)aminonitrobenzene,
2-amino-4-methyl-5-N-($\beta$-hydroxyethyl)aminonitrobenzene,
2-amino-4-methyl-5-N-methylaminonitrobenzene,
2-N-($\beta$-hydroxyethyl)amino-5-methoxynitrobenzene,
2-amino-5-($\beta$-hydroxyethyloxy)nitrobenzene,
2-N-($\beta$-hydroxyethyl)aminonitrobenzene,
3-amino-4-N-($\beta$-hydroxyethyl)aminonitrobenzene,
3-($\beta$-hydroxyethyloxy)-4-N-($\beta$-hydroxyethyl)aminonitrobenzene,
2-N-methylamino-4-($\beta$,$\gamma$-dihydroxypropyloxy)nitrobenzene,
2-N-($\beta$-hydroxyethyl)amino-5-($\beta$-hydroxyethyloxy)nitrobenzene,
2-N-($\beta$-hydroxyethyl)amino-5-($\beta$,$\gamma$-dihydroxypropyloxy)nitrobenzene,
3-hydroxy-4-N-($\beta$-hydroxyethyl)aminonitrobenzene,
3-N-($\beta$-hydroxyethyl)amino-4-N-($\beta$-hydroxyethyl)aminonitrobenzene,
2-amino-4-methyl-5-N-($\beta$,$\gamma$-dihydroxypropyl)aminonitrobenzene,
2-amino-4-methyl-5-hydroxynitrobenzene,
2-N-($\beta$-aminoethyl)amino-4-methoxynitrobenzene,
2-N-($\beta$-aminoethyl)aminonitrobenzene,
2-N-($\beta$-aminoethyl)amino-5-N-($\beta$-hydroxyethyl)aminonitrobenzene,
2-amino-4-methyl-5-N-($\beta$-aminoethyl)aminonitrobenzene, and
2-amino-4-chloro-5-N-($\beta$-aminoethyl)aminonitrobenzene.

The dye compositions according to the invention may comprise, as a suitable carrier, water and/or organic solvents which are acceptable in cosmetics, and especially alcohols such as ethyl alcohol, isopropyl alcohol, benzyl alcohol and phenyl ethyl alcohol, or glycols or glycol ethers such as, for example, ethylene glycol and its monomethyl, monoethyl and monobutyl ethers, propylene glycol, butylene glycol, dipropylene glycol, and diethylene glycol alkyl ethers such as, for example, diethylene glycol monoethyl ether or monobutyl ether, in concentrations of between 0.5 and 20% and, preferably, between 2 and 10% by weight relative to the total weight of the composition.

Fatty amides such as the mono- and diethanolamides of acids derived from copra, of lauric acid or of oleic acid can also be added to the composition according to the invention at concentrations of between 0.05 and 10% by weight.

Anionic, cationic, nonionic or amphoteric surface-active agents, or their mixtures, can also be added to the composition according to the invention. The surfactants are preferably present in the composition according to the invention in a proportion of between 0.1 and 50% by weight, and advantageously between 1 and 20% by weight, relative to the total weight of the composition.

Among the surface-active agents, more particular mention can be made of the anionic surface-active agents used by themselves or mixed, such as, particularly, the alkali metal salts, the magnesium salts, the ammonium salts, the amine salts and the alkanolamine salts of the following compounds:
alkylsulphates, alkyl ether sulphates, alkylamidesulphates, ethoxylated or otherwise, alkylsulphonates, alkylamidesulphonates and alpha-olefinsulphonates;
alkylsulphoacetates;
fatty acids such as lauric, myristic, oleic, ricinoleic, palmitic and stearic acids, copra oil acids or hydrogenated copra oil acids, and polyglycol ether carboxylic acids, the alkyl radicals of these compounds having a linear chain containing 12 to 18 carbon atoms.

As cationic surface-active agents, special mention may be made of the salts of fatty amines, the quaternary ammonium salts such as alkyldimethylbenzylammonium, alkyltrimethylammonium, alkyldimethylhydroxyethylammonium and dimethyldialkylammonium chlorides and bromides, alkylpyridinium salts, and imidazoline derivatives. The alkyl groups in the abovementioned quaternary ammonium derivatives are straight-chain groups, preferably containing from 12 to 18 carbon atoms.

Amine oxides can also be mentioned among these compounds of a cationic nature.

Among the amphoteric surface-active agents which can be employed, special mention can be made of alkylamino (mono- and di-) propionates, betaines such as alkylbetaines, N-alkylsulphobetaines, and N-alkylaminobetaines, their alkyl radicals containing from 1 to 22 carbon atoms, and cycloimidiniums such as alkylimidazolines.

Among the nonionic surfactants which can optionally be used in the composition according to the invention, there may be mentioned the products of condensation of a mono alcohol, an $\alpha$-diol, an alkylphenol or an amide with glycidol or a glycidol precursor, such as the compounds corresponding to the following formulae:

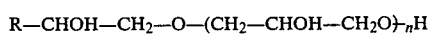

in which R denotes an aliphatic, alicyclic or arylaliphatic radical containing 7 to 21 carbon atoms, and their mixtures, the aliphatic chains being capable of containing ether, thioether and hydroxymethylene groups, and n being an integer such that $1 \leq n \leq 10$;

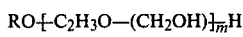

in which R denotes an alkyl, alkenyl or alkylaryl radical containing 8 to 22 carbon atoms, and $1 \leq m \leq 10$; polyethoxylated or polyglycerolated fatty alcohols, alkylphenols or acids containing a linear $C_8C_{18}$ fatty chain; condensates of ethylene oxide and propylene oxide with fatty alcohols;
polyethoxylated fatty amides containing at least 5 moles of ethylene oxide; and polyethoxylated fatty amines.

The thickening products which can be added to the composition according to the invention can be advantageously taken from the group consisting of sodium alginate, gum arabic, guar gum, cellulose derivatives such as methylcellulose, hydroxyethylcellulose, hydroxypropylmethylcellulose, the sodium salt of carboxymethylcellulose and acrylic acid polymers.

Inorganic thickening agents such as bentonite can also be used. These thickeners are used by themselves or mixed and, preferably, are present in a proportion of between 0.5 and 5% by weight relative to the total weight of the composition and, advantageously, between 0.5 and 3% by weight.

The dye compositions according to the invention may be formulated at an acid, neutral or alkaline pH, the pH being capable of ranging from 4 to 10.5 and, preferably, from 6 to 10. Alkanolamines and alkali metal or ammonium hydroxides and carbonates can be mentioned among the alkalifying agents which can be used. Lactic acid, acetic acid, tartaric acid, phosphoric acid, hydrochloric acid and citric acid can be mentioned among the acidifying agents.

The dye compositions can also contain various usual adjuvants such as perfumes, sequestering agents, film-forming products and processing agents, dispersing agents, hair-conditioning agents, preserving agents, opacifiers, as well as any other adjuvant usually employed in cosmetics.

The dye composition according to the invention may be presented in the various conventional forms for dyeing hair, such as thickened or gelled liquids, creams, aerosol foams or any other suitable forms for dyeing keratinic fibres.

The composition according to the invention can also be presented in the form of a hairsetting lotion intended both to impart a slight colour to the hair and to improve the set behaviour.

In this case, it is presented in the form of a hydroalcoholic solution containing at least one cosmetic resin, and it is applied to wet hair which has previously been washed and rinsed and which is then curled and dried.

The cosmetic resins used in hairsetting lotions can be, especially, polyvinylpyrrolidone, crotonic acid/vinyl acetate, vinylpyrrolidone/vinylacetate, maleic anhydride/butyl vinyl ether, and maleic anhydride/methyl vinyl ether copolymers. These cosmetic resins are present in the compositions of the invention in a proportion of 1 to 3% by weight, and preferably 1 to 2% by weight, based on the total weight of the composition.

Another subject of the present invention is a new process for dyeing keratinic fibres and especially human hair, characterized in that the dye composition defined above is allowed to act on dry or wet keratinic fibres. The compositions according to the invention can be used as unrinsed lotions, that is to say that the compositions according to the invention are applied to the keratinic fibres which are then dried without intermediate rinsing. In other application embodiments the dye compositions according to the invention are applied to the keratinic fibres for an application time ranging from 3 to 60 minutes, preferably from 5 to 45 minutes, and the hair is then rinsed, washed if appropriate, rinsed again and dried.

The dye compositions according to the invention can be applied to natural or dyed, permanent-waved or unwaved hair, or to strongly or slightly bleached, and optionally permanent-waved, hair.

To make the subject of the invention understood better, several embodiments will now be described by way of examples which are purely illustrative and which do not imply any limitation.

EXAMPLE 1

The following dye composition is prepared:

| | |
|---|---|
| 5-nitrovanillin | 0.10 g |
| 2-N—methylamino-5-[N,N—bis($\beta$-hydroxyethyl)amino]nitrobenzene | 0.30 g |
| 2-N—methylamino-4-($\beta,\gamma,\alpha$-dihydroxypropyloxy)nitrobenzene | 0.10 g |
| 2-N—($\beta$-hydroxyethyl)amino-5-($\beta,\gamma$- dihydroxypropyloxy)nitrobenzene | 0.15 g |
| nonylphenol containing 9 moles of ethylene oxide | 8.00 g |
| lauroyl diethanolamide | 2.00 g |
| 2-ethoxyethanol | 10.00 g |
| 2-amino-2-methyl-1-propanol q.s. pH 9 | |
| demineralized water q.s. | 100.0 g |

Blonde hair is impregnated with this composition for 30 minutes. It is rinsed. The dry hair then has a pearlescent dark-blond shade.

EXAMPLE 2

The following dye composition is prepared:

| | |
|---|---|
| 5-nitrovanillin | 0.10 g |
| 2-amino-4-methyl-5-N—($\beta$-hydroxyethyl)aminonitrobenzene | 0.15 g |
| Celliton extra blue (BASF) | 0.05 g |
| 3-N—($\beta$-hydroxyethyl)amino-4-N—($\beta$-hydroxyethyl)aminonitrobenzene | 0.10 g |
| BSNZ diazoacetoquinone black (ICI Francolor) | 0.05 g |
| nonylphenol containing 9 moles of ethyle oxide | 8.00 g |
| lauroyl diethanolamide | 2.00 g |
| 2-ethoxyethanol | 10.00 g |
| 2-amino-2-methyl-1-propanol q.s pH 9 | |
| demineralized water q.s. | 100.00 g |

This composition is applied to blonde hair. After 30 minutes' application, the hair is rinsed and dried. The hair is then dyed in a coppery dark blonde shade.

EXAMPLE 3

The following dye composition is prepared:

| | |
|---|---|
| 5-nitrovanillin | 0.05 g |
| 2-N—($\beta$-hydroxyethyl)amino-5-[N,N—bis($\beta$-hydroxyethyl)amino]nitrobenzene | 0.35 g |
| 2-N—methylamino-4-($\beta$-hydroxyethyloxy)nitrobenzene | 0.07 g |

-continued

| | |
|---|---|
| 2-amino-5-N—(β-hydroxyethyl)aminonitrobenzene | 0.05 g |
| lauric acid | 1.00 g |
| oleoyl diethanolamide | 3.00 g |
| 2-butoxyethanol | 5.00 g |
| Ethomeen HT 60 (AKZO) | 3.50 g |
| Cellosize WP 03 H (Union Carbide) | 2.00 g |
| 2-amino-2-methyl-1-propanol q.s. pH 9.5 | |
| demineralized water q.s. | 100.00 g |

This composition is a thickened liquid which is applied to chestnut-brown hair for 20 minutes. The excess product is then removed by rinsing and the hair is dried.

The latter is then dyed in a purple-violet chestnut-brown shade.

EXAMPLE 4

The following dye composition is prepared:

| | |
|---|---|
| 5-nitrovanillin | 0.10 g |
| 2-N—methylamino-5-[N—methyl-N—(β-hydroxyethyl)amino]nitrobenzene | 0.20 g |
| 2-N—β-hydroxyethylamino-5-[N—methyl-N—(β-hydroxyethyl)amino]nitrobenzene | 0.25 g |
| 3-methoxy-4-N—(β-hydroxyethyl)aminonitrobenzene | 0.10 g |
| 2-amino-3-hydroxynitrobenzene | 0.20 g |
| 3-N—(β-hydroxyethyl)amino-4-N—(β-hydroxyethyl)aminonitrobenzene | 0.15 g |
| oleoyl diethanolamide | 3.00 g |
| 2-butoxyethanol | 5.00 g |
| Ethomeen HT 60 | 3.50 g |
| lauric acid | 1.00 g |
| Cellosize WP 03 H (Union Carbide) | 2.00 g |
| 2-amino-2-methyl-1-propanol q.s. pH 9.5 | |
| demineralized water q.s | 100.00 g |

This formulation is presented in the form of a thickened liquid.

The latter is applied to light chestnut-brown hair for an application time of 30 minutes. After rinsing and drying, this hair has a golden chestnut-brown shade.

EXAMPLE 5

The following dye composition is prepared:

| | |
|---|---|
| 5-nitrovanillin | 0.05 g |
| 2-amino-5-hydroxynitrobenzene | 0.45 g |
| 2-N—(β-hydroxyethyl)amino-5-hydroxynitrobenzene | 0.52 g |
| $C_{12-14}$ fatty alcohol ethoxylated with 12 moles of ethylene oxide | 10.00 g |
| hydroxyethylcellulose sold by the Hercules company under the name Natrosol 250 HHR | 0.20 g |
| tetradecyltrimethylammonium bromide | 1.00 g |
| aqueous ammonia containing 20% of $NH_3$ q.s. pH 6 | |
| demineralized water q.s. | 100.00 g |

This composition is applied to chestnut-brown hair and is left applied for 30 minutes.

After rinsing and drying, a shade with a coppery glint is obtained on this hair.

EXAMPLE 6

| | |
|---|---|
| 5-nitrovanillin | 0.10 g |
| vinylacetate/crotonic acid (90/10) copolymer | 1.80 g |
| vinylpyrrolidone/vinylacetate (60/40) copolymer | 0.40 g |
| ethyl alcohol q.s. 50 g alcohol | |
| triethanolamine q.s. pH 7 | |
| demineralized water q.s. | 100.00 g |

This hair setting lotion is applied to light blonde hair. After drying, the hair is coloured in a golden light-blonde shade.

We claim:

1. A composition for dyeing keratinic fibers comprising in a cosmetically acceptable carrier
   (a) a tinctorially effective amount of 5-nitrovanillin of the formula

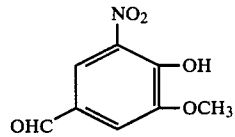

(I)

and
   (b) at leat one violet or blue nitrobenzene dye of the formula

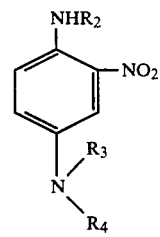

(II)

wherein $R_2$ represents hydrogen, lower alkyl containing 1-4 carbon atoms, monohydroxyalkyl wherein the alkyl moiety contains 1-4 carbon atoms or polyhydroxyalkyl wherein the alkyl moiety contains 2-4 carbon atoms and $R_3$ and $R_4$ each independently represent lower alkyl containing 1-4 carbon atoms, monohydroxyalkyl wherein the alkyl moiety contains 1-4 carbon atoms or polyhydroxyalkyl wherein the alkyl moiety contains 2-4 carbon atoms, said violet or blue nitrobenzene dye being present in an amount ranging from 0.01 to 5 percent by weight based on the total weight of said composition.

2. The composition of claim 1 wherein said 5-nitrovanillin is present in an amount ranging from 0.01 to 1 percent by weight based on the total weight of said composition.

3. The composition of claim 1 wherein said violet or blue nitrobenzene dye is selected from the group consisting of
   2-(N-methyl)amino-5-[N,N-bis(β-hydroxyethyl)amino]nitrobenzene,
   2-(N-methyl)amino-5-[N-methyl-N-(β-hydroxyethyl)-amino]nitrobenzene,
   2-(N-β-hydroxyethyl)amino-5-[N,N-bis(β-hydroxyethyl)-amino]nitrobenzene,
   2-(N-β-hydroxyethyl)amino-5-[N-methyl-N-(β-hydroxyethyl)amino]nitrobenzene,
   2-(N-γ-hydroxypropylamino)-5-(N,N-bis(β-hydroxyethyl)amino]nitrobenzene, 2-(N-methylamino)-5-(N-methyl-N-(β,γ-dihydroxypropyl)amino]nitrobenzene, and 2-amino-5-[N,N-bis(β-hydroxyethyl)amino]nitrobenzene.

4. The composition of claim 1 which also contains a tinctorially effective amount of a direct dye, other than those of Formulas I and II, selected from the group consisting of an azo dye, an aminoanthraquinone dye, a metallized dye, a triarylmethane dye and an indamine dye.

5. The composition of claim 4 wherein said direct dye other than those of Formulas I and II is present in an amount ranging from 0.001 to 10 percent by weight based on the total weight of said composition.

6. The composition of claim 1 wherein said cosmetically acceptable carrier is water, a cosmetically acceptable organic solvent or a mixture thereof, said organic solvent being selected from the group consisting of an alcohol, a glycol and a glycol ether and being present in an amount ranging from 0.5 to 20 percent by weight based on the total weight of said composition.

7. The composition of claim 6 wherein said organic solvent is present in an amount ranging from 2 to 10 percent by weight based on the total weight of said composition.

8. The composition of claim 1 which also contains a fatty amide present in an amount ranging from 0.05 to 10 percent by weight based on the total weight of said composition.

9. The composition of claim 1 which also contains an anionic, cationic, nonionic or amphoteric surface-active agent, or mixtures thereof, present in an amount ranging from 0.1 to 50 percent by weight based on the total weight of said composition.

10. The composition of claim 9 wherein said surface-active agent is present in an amount ranging from 1 to 20 percent by weight based on the total weight of said composition.

11. The composition of claim 1 which also contains a thickener present in an amount ranging from 0.5 to 5 percent by weight based on the total weight of said composition.

12. The composition of claim 11 wherein said thickener is present in an amount ranging from 0.5 to 3 percent by weight based on the total weight of said composition.

13. The composition of claim 1 which also contains an effective amount of one or more of a perfume, a sequestering agent, a film-forming agent, a processing agent, a dispersing agent, a hair-conditioning agent, a preserving agent and an opacifying agent.

14. The composition of claim 1 having a pH ranging from 4 to 10.5.

15. The composition of claim 1 having a pH ranging from 6 to 10.

16. The composition of claim 1, in the form of a hair setting lotion, containing at least one cosmetic resin present in an amount ranging from 1 to 3 percent by weight based on the total weight of said composition.

17. The composition of claim 16 wherein said cosmetic resin is present in an amount ranging from 1 to 2 weight percent based on the total weight of said composition.

18. A process for dyeing keratinic fibers comprising applying to wet or dry keratinic fibers, in an amount effective to dye said keratinic fibers, a composition comprising in a cosmetically acceptable carrier a tinctorially effective amount of 5-nitrovanillin of the formula

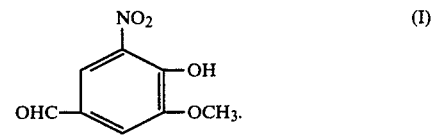

19. A process for dyeing keratinic fibers comprising applying to keratinic fibers, in an amount effective to dye said keratinic fibers, a composition comprising in a cosmetically acceptable carrier a tinctorially effective amount of 5-nitrovanillin of the formula

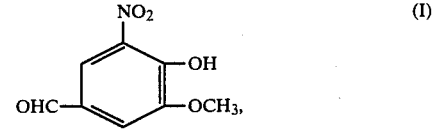

permitting said composition to remain in contact with said fibers for a period of time ranging from 3 to 60 minutes, rinsing said fibers and drying said fibers.

20. The process of claim 19 wherein said composition is permitted to remain in contact with said fibers for a period of time ranging from 5 to 45 minutes.

* * * * *